United States Patent
Miethke

(10) Patent No.: US 9,155,871 B2
(45) Date of Patent: Oct. 13, 2015

(54) ELECTRICALLY OPERABLE, IN ONE POSSIBLE EMBODIMENT PROGRAMMABLE HYDROCEPHALUS VALVE

(71) Applicant: C.MIETHKE GMBH & CO KG, Potsdam (DE)

(72) Inventor: Christoph Miethke, Potsdam (DE)

(73) Assignee: C. MIETHKE GMBH & CO KG (DE)

( * ) Notice: Subject to any disclaimer, the term of this patent is extended or adjusted under 35 U.S.C. 154(b) by 96 days.

(21) Appl. No.: 13/895,619

(22) Filed: May 16, 2013

(65) Prior Publication Data

US 2014/0005588 A1 Jan. 2, 2014

Related U.S. Application Data

(63) Continuation-in-part of application No. PCT/EP2011/005819, filed on Nov. 18, 2011.

(30) Foreign Application Priority Data

Nov. 19, 2010 (DE) .................. 10 2010 051 743

(51) Int. Cl.
*A61M 27/00* (2006.01)
*F16K 99/00* (2006.01)

(52) U.S. Cl.
CPC .......... *A61M 27/006* (2013.01); *A61M 27/002* (2013.01); *A61M 2202/0464* (2013.01); *A61M 2210/0687* (2013.01);
(Continued)

(58) Field of Classification Search
CPC ........ A61B 5/03; A61B 5/031; A61B 5/0031; A61M 27/006; A61M 27/002; A61M 5/14276; A61M 2210/0687; A61M 2210/0693; A61M 2202/0464; A61M 2205/04; F16K 31/0682; F16K 11/052; F16K 31/10; F16K 11/044; F16K 11/14; F16K 11/16; F16K 31/0658; F16K 31/0662; F16K 7/14; F16K 7/16; F16K 7/17

See application file for complete search history.

(56) References Cited

U.S. PATENT DOCUMENTS 3,570,807 A * 3/1971 Sturman et al. .................. 251/65
4,461,968 A 7/1984 Kolm et al.
(Continued)

FOREIGN PATENT DOCUMENTS

DE 616458 7/1935
DE 2208229 8/1973
(Continued)

*Primary Examiner* — Adam Marcetich
(74) *Attorney, Agent, or Firm* — Nils H. Ljungman & Associates

(57) ABSTRACT

An electrically operable, in one possible embodiment programmable hydrocephalus valve. The abstract of the disclosure is submitted herewith as required by 37 C.F.R. §1.72(b). As stated in 37 C.F.R. §1.72(b): A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

18 Claims, 4 Drawing Sheets

(52) U.S. Cl.
CPC ... *A61M 2210/0693* (2013.01); *F16K 99/0003* (2013.01); *F16K 99/0005* (2013.01); *F16K 99/0007* (2013.01)

(56) References Cited

U.S. PATENT DOCUMENTS

| | | | |
|---|---|---|---|
| 4,567,394 A | | 1/1986 | Frisch |
| 5,314,164 A | * | 5/1994 | Smith ................... 251/129.17 |
| 5,343,894 A | * | 9/1994 | Frisch et al. ............ 137/625.65 |
| 5,582,590 A | * | 12/1996 | Hauser et al. ................ 604/30 |
| 5,593,134 A | | 1/1997 | Steber et al. |
| 5,660,207 A | * | 8/1997 | Mudd ..................... 137/599.13 |
| 5,799,696 A | | 9/1998 | Weiss |
| 5,902,253 A | | 5/1999 | Pfeiffer et al. |
| 6,443,174 B2 | * | 9/2002 | Mudd ............................ 137/10 |
| 6,588,727 B2 | | 7/2003 | Christoffersen et al. |
| 8,123,196 B1 | * | 2/2012 | Chernoff ........................ 251/228 |
| 2002/0026138 A1 | * | 2/2002 | Cowan et al. ..................... 604/8 |
| 2002/0052563 A1 | * | 5/2002 | Penn et al. ..................... 600/561 |
| 2003/0057393 A1 | | 3/2003 | Christoffersen et al. |
| 2004/0024346 A1 | * | 2/2004 | Miethke ............................. 604/9 |
| 2005/0038371 A1 | * | 2/2005 | Reich et al. ....................... 604/9 |
| 2005/0071001 A1 | * | 3/2005 | Jarvik ........................... 623/3.28 |
| 2007/0112328 A1 | * | 5/2007 | Steinbach et al. ............. 604/500 |
| 2007/0156190 A1 | * | 7/2007 | Cinbis ................................ 607/5 |
| 2007/0163541 A1 | * | 7/2007 | Schweinfurth et al. ....... 123/396 |
| 2009/0299421 A1 | * | 12/2009 | Sawchuk ........................... 607/4 |
| 2009/0309055 A1 | * | 12/2009 | Scheibe ........................ 251/228 |

FOREIGN PATENT DOCUMENTS

| | | |
|---|---|---|
| DE | 3127882 | 2/1983 |
| DE | 3300717 | 8/1983 |
| DE | 3400645 | 7/1984 |
| DE | 3528072 | 2/1987 |
| DE | 3533085 | 3/1987 |
| DE | 4307387 | 9/1994 |
| DE | 29507380 | 8/1995 |
| DE | 4420741 | 12/1995 |
| DE | 4425078 | 1/1996 |
| DE | 29613521 | 9/1996 |
| DE | 19522806 | 1/1997 |
| DE | 29718306 | 1/1998 |
| DE | 19650116 | 4/1998 |
| DE | 69408166 | 7/1998 |
| DE | 19720482 | 11/1998 |
| DE | 19737173 | 3/1999 |
| DE | 29822959 | 5/1999 |
| DE | 29902923 | 7/1999 |
| DE | 19854508 | 5/2000 |
| DE | 19946003 | 5/2000 |
| DE | 19922612 | 12/2000 |
| DE | 29824447 | 2/2001 |
| DE | 10038522 | 3/2001 |
| DE | 20009969 | 10/2001 |
| DE | 10104017 | 6/2002 |
| DE | 10105315 | 6/2002 |
| DE | 10101796 | 7/2002 |
| DE | 10120709 | 10/2002 |
| DE | 69710486 | 10/2002 |
| DE | 10121395 | 11/2002 |
| DE | 10233316 | 2/2003 |
| DE | 10202996 | 8/2003 |
| DE | 10210211 | 9/2003 |
| DE | 20121938 | 9/2003 |
| DE | 69812767 | 1/2004 |
| DE | 10306683 | 9/2004 |
| DE | 69827952 | 3/2005 |
| DE | 69922288 | 5/2005 |
| DE | 202005010075 | 10/2005 |
| DE | 60110533 | 1/2006 |
| DE | 102004023554 | 1/2006 |
| DE | 102004036358 | 2/2006 |
| DE | 69733125 | 3/2006 |
| DE | 60018425 | 4/2006 |
| DE | 60209449 | 10/2006 |
| DE | 60028818 | 11/2006 |
| DE | 60116758 | 11/2006 |
| DE | 102006005517 | 3/2007 |
| DE | 60118540 | 5/2007 |
| DE | 102006036014 | 6/2007 |
| DE | 202006006862 | 8/2007 |
| DE | 602004002407 | 9/2007 |
| DE | 102007035721 | 2/2009 |
| DE | 602005004782 | 2/2009 |
| DE | 102008042071 | 3/2009 |
| DE | 202009000593 | 3/2009 |
| DE | 102007050407 | 4/2009 |
| DE | 102007059300 | 6/2009 |
| DE | 202009007298 | 9/2009 |
| DE | 112008000862 | 3/2010 |
| DE | 202009016447 | 3/2010 |
| EP | 0172304 | 2/1986 |
| EP | 0191011 | 8/1986 |
| EP | 0538236 | 4/1993 |
| EP | 0565610 | 10/1993 |
| EP | 0693788 | 1/1996 |
| EP | 0741248 | 11/1996 |
| EP | 0884511 | 12/1998 |
| EP | 0915277 | 5/1999 |
| EP | 0943811 | 9/1999 |
| EP | 1380317 | 1/2004 |
| EP | 2008683 | 12/2008 |
| FR | 2324967 | 4/1977 |
| WO | WO 02/092993 | 11/2002 |
| WO | WO 2007/000321 | 1/2007 |
| WO | WO 2007/081888 | 7/2007 |

* cited by examiner

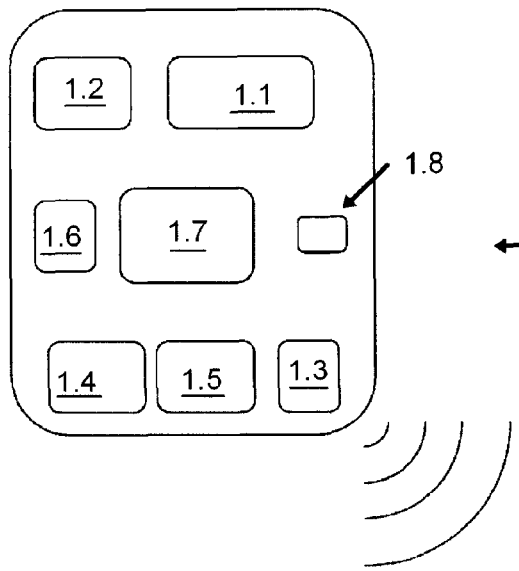

FIG. 1A

1.0 Steuergerät
1.1 Anzeige
1.2 Batterie
1.3 Telemetrie
1.4 USB/COM Interface
1.5 USB Speicher
1.6 RF Interface
1.7 Controller
1.8 Absolutedrucksensor 1.0 Control Device
1.1 Display
1.2 Battery
1.3 Telemetry
1.4 USB/COM interface
1.5 USB memory
1.6 RF interface
1.7 Controller
1.8 Absolute pressure sensor

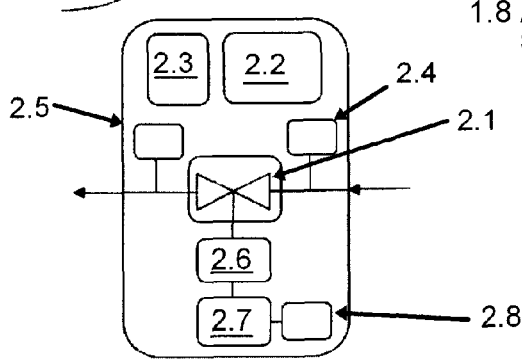

FIG. 1B

2.0 Implantat
2.1 Piezoventil
2.2 Batterie
2.3 Telemetrie
2.4 Eingangsdruck
2.5 Ausgangsdruck
2.6 HV-Stufe
2.7 Controller
2.8 Neigung 2.0 Implant
2.1 Piezo valve
2.2 Battery
2.3 Telemetry
2.4 Inlet pressure
2.5 Outlet pressure
2.6 HV step
2.7 Controller
2.8 Inclination Energieversorgung (induktiv, Batterie) — Power supply (inductive, battery)
Lagesensor — Posture sensor
Telemetrisches Module — Telemetric module
Drucksensor E — Pressure sensor E
Datenspeicher — Memory
Drucksensor A — Pressure sensor A
Aktor (Piezo) — Actuator (piezo)
Steuerung/CPU — Control/CPU

ELECTRICALLY OPERABLE, IN ONE POSSIBLE EMBODIMENT PROGRAMMABLE HYDROCEPHALUS VALVE

CONTINUING APPLICATION DATA

This application is a Continuation-In-Part application of International Patent Application No. PCT/EP2011/005819, filed on Nov. 18, 2011, which claims priority from Federal Republic of Germany Patent Application No. 10 2010 051 743.7, filed on Nov. 19, 2010. International Patent Application No. PCT/EP2011/005819 was pending as of the filing date of this application. The United States was an elected state in International Patent Application No. PCT/EP2011/005819.

BACKGROUND

1. Technical Field

The present application relates to an electrically operable, in one possible embodiment programmable hydrocephalus valve.

2. Background Information

Background information is for informational purposes only and does not necessarily admit that subsequently mentioned information and publications are prior art.

People suffering from hydrocephalus have the problem that an increased internal pressure on the brain resulting from excess cerebrospinal fluid (liquor cerebrospinalis) leads to serious problems for the persons concerned. The brain tissue thus becomes damaged and permanently broken down and different symptoms appear, such as dizziness, gait disorders, headaches, nausea, vomiting and dementia. If untreated, the disease can eventually be fatal. The nature and extent of the symptoms that arise depend on the underlying causes of the disease, the general constitution, but mainly on the age of the patient. In babies the pressure increase causes an unnatural growth of the head, in adults the brain substance disappears more quickly in favor of the water content inside the skull.

A successful treatment possibility for persons suffering from hydrocephalus has been available since the 1950s. An artificial drainage is implanted which enables the cerebrospinal fluid to drain away into other regions of the body, in which the diverted liquid can then be dissipated. The drainage can be controlled by means of valves that are intended to essentially ensure or promote the required and/or desired pressure inside the skull. Since then a plurality of various technical solutions have been proposed which extend the treatment possibilities or that are intended, however, to prevent or limit complications that frequently arise.

Various types of valve have been launched on the market up to now and can be sub-divided according to their functional principle as follows:

|  | permanent | adjustable |
| --- | --- | --- |
| 1. Differential pressure valves |  |  |
| a: Silicone slit valve | ✓ | x |
| b: Membrane valve | ✓ | x |
| c: Ball-in-cone valve | ✓ | ✓ |
| 2. Hydrostatic valves |  |  |
| a: Anti-siphon valve | ✓ | x |
| b: Liquid control | ✓ | x |
| c: Gravitational valve | ✓ | ✓ |

✓ = available
x = not available

The rigid differential pressure valve of group 1 can be proposed as a silicone slit valve, as a membrane valve or as a ball-in-cone construction (U.S. Pat. No. 5,069,663, DE 30 20 991, US 20100010415). The valves in their opening characteristics are developed for the supine position of the patient. In the standing position these valves systematically lead to over-drainage, i.e. to un-physiologically low negative pressure in the head of the patient and can lead to severe complications. Valves with a complicated construction for the differential pressure and which fulfil their function in both the supine and standing position have as yet been unable to find any practical application (DE102009009880). A fundamental improvement in the characteristics of differential pressure valves results from the possibility of being able to percutaneously control the opening characteristics (U.S. Pat. No. 4,772,257, EP 0421557 A2, U.S. Pat. No. 5,928,182, EP 135991 A1, G8 2143008 A, U.S. Pat. No. 4,551,128, EP 0060369). In an enhancement of this, approaches are known, in which the adjustment can be electrically driven and supported by the use of sensors (EP2008683). The adjustment enables the valve function to be individually matched to the specific patients. This possibility exists for valves of the group 1-c, although the dependence of the physical behavior in the drainage system on the position of the patient is not solved here either. If the valves are adjusted to a low opening pressure, this will indeed on the one hand favor the clinical result, on the other hand the danger of over-drainage in the standing position is simultaneously and/or substantially simultaneously dramatically increased. Conversely, the adjustment to a very high value can indeed reduce the danger of over-drainage, thereby strongly negatively influencing the desired clinical result, as the now required and/or desired opening pressure in the supine position will be significantly too high.

Valves of the second group redress this. Hydrostatic valves are configured to take into account the changes in the physical conditions in the drainage system brought about by a positional shift. Three different principles are used for this.

The oldest design was realized in the "anti-siphon device". Up to now a plurality of different designs based on the same principle have been commercialized (EP 0670740 B1, U.S. Pat. No. 5,800,376, DE 27 52 087). The effect of the negative pressure on the outlet of the valve is systematically minimized by this means. However, this feature is offset by the serious drawback that the subcutaneous pressure around the valve housing exercises a considerable influence on the mode of operation of the valve. Tissue growth or an unfavorable position of the patient can cause this pressure to vary considerably and even lead to the valve closing completely or substantially completely. These valves have also been unable to supersede the conventional valves (Drake, Toronto).

The same is true for the principle of flow control. Flow-regulating valves are intended to essentially ensure and/or promote that the drainage rate is held constant or substantially constant independently of the differential pressure acting on the valve. Whereas the drainage rate in conventional valves increases in proportion to the acting pressure differential, this is essentially prevented and/or minimized in flow-regulating valves (Siphonguard [Codman], Orbis Sigma Valve [Cordis], Diamond Valve [Phoenix]; EP 798012 A1, U.S. Pat. No. 4,627,832, U.S. Pat. No. 4,776,838). The average natural production of liquor is 23 ml/h. In practice, flow-regulating systems have the following problems:

Up to now it has been technically impossible to essentially ensure and/or promote the permissible drainage rate value. Variances in the context of the production process remain too large (Aschoff, Schoener).

The natural variance of production remains systematically ignored. If the individual values are too high or too low, then this can lead to over-drainage as well as to under-drainage.

The flow regulation is controlled by extremely small cross sections on the opening mechanism. Particles in the liquor such as for example cellular components exert a dramatic effect on the function and can very easily block the valve up. International comparative studies have shown that this principle could not improve the treatment results of the hydrocephalus (Drake et al).

The gravity assisted valves are offered on the market in two variants. In the first approach, the flow control is effected by gravitationally controlled switching of two valves arranged in parallel or substantially parallel (DE 4401422, DE 4307387). The design therefore sets up two different pressure situations in the ventricular system of the patient as a function of the patient's posture. In the second approach, the weight of balls is exploited in order to set up an opening pressure that is modifiable as a function of the body position (EP 0617975, EP 0115973, DE 19535637). A gravity valve that is equipped with a percutaneously adjustable gravitation unit has recently become available (WO 2005092424). For the first time the technology enables individual adjustments contingent on body growth or on the increase in peritoneal pressure The function of the ventricular drainage for hydrocephalus comprises on the one hand in draining away cerebrospinal fluid so as to essentially prevent and/or minimize the pathological pressure increase, and on the other hand, however, an unwanted high drainage and the extremely negative pressure resulting therefrom should be similarly essentially prevented and/or minimized. In previously available valves, this has been attempted on the basis of a pressure differential valve. Depending on the design, other influential factors are the position of the patient, the subcutaneous pressure or the viscosity of the cerebrospinal fluid. The differential pressure between the ventricle of the cerebrum and drainage medium (atrium, free abdominal cavity) is determinant for the drainage. However, very different situations can now lead to an increased pressure difference between the ventricle of the cerebrum and drainage medium. It could be that a large amount of cerebrospinal fluid had been produced; however it may also simply be that an increased pressure rise may have been caused by a change in position from the horizontal to the vertical. In the first case a valve has to open or should open, in the second case this should not occur. However, for a differential pressure valve, the situation is identical in both cases. Gravitation valves offer the best options but also in this case they are unable to react to temporarily modified situations, such as for example abdominal cavity pressure. Clinically unsatisfactory results can be illustrated by both over- as well as under-drainage. It often remains to be seen whether an optimal treatment success could have been possible.

Although the described valve systems have been able to solve many problems, the following aspects remain unsolved:

1. Matching the valve characteristics to growth- or age-dependent changes or other changes in the physiological boundary conditions 2. Non-invasive, selective adjustment of the valve characteristics with different set points for differing body positions of the patient 3. Consistent or substantially consistent therapy of patients up to the removal of the drainage that has perhaps become superfluous 4. Appropriate adjustment of the liquor drainage to individual specificities 5. Previously offered solutions are exclusively based on the differential pressure principle. Other parameters that could likewise impact the meaningful control of the liquor drainage are not addressed 6. Intelligent, situation-dependent control of valve characteristics 7. Subsequent analyses of incidents. The explanation of the incidents generally remains at the level of assumptions.

To solve these various problems, approaches have been made that are intended to implement controls adapted to them with the help of new valve processes (DE 19915558, DE 19654990, DE 10233601, WO 2010066438).

Proven valve technologies include spring-loaded ball valves, whose spring is adjustable. Different mechanical devices can be used for the adjustment. One possible adjustment device is formed by a rotor that is rotatably arranged in the valve. The periphery of the rotor is provided with a sliding surface, on which the spring rests directly or indirectly, such that an adjustment of the rotor causes an adjustment of the spring (DE102005013720, DE102007059300).

Another known valve technology also uses a rotor to adjust the spring. However, the rotor does not have a curved outside surface but rather has surfaces like screw flights or screw threads, on which the spring slides. This surface is mostly stepped (U.S. Pat. No. 7,235,060, U.S. Pat. No. 7,559,912, US2010/0010415).

The rotor is mostly pre-set using magnets, wherein part of the magnets are arranged in the rotor and implanted with the valve under the skin of the patient and wherein the other part of the magnet is rotated on the head of the patient above the rotor. This causes the magnets of the rotor to turn with the rotor.

However, there are other known proposals for adjusting the rotor, for example with a drive motor or with an electromechanical actuator. In this regard, electric motors, magnets and linear drives are concerned (EP2008683).

The valve switch in known embodiments is therefore operated electromechanically, electromagnetically, but in another embodiment also by exploiting the properties of shape memory materials. Problems result here in energy consumption and in the generation of heat as well as in biocompatibility, thereby making the constructions very complex. As far as is known, a programmable valve has not been offered on the market.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

OBJECT OR OBJECTS

An object of the present application is an appropriate and patient-friendly programming, such that better perspectives for treatment, optionally also new perspectives for treatment, are provided. The above described problems should be solved and new therapy approaches enabled by means of an appropriate and patient-friendly programming of the valve characteristics.

SUMMARY

In this regard, the possible embodiments of the present application may show:

a) a valve that can be actuated at least partially independently of the liquor pressure b) an electrically actuated actuator for operating the valve, for example a piezoelectric actuator (translator), c) a processor and a data storage unit d) an energy source (battery)

The possible embodiments may also be functional without a separate locking device, as for example is the subject matter of EP 1 380 317 A1. EP 1 380 317 solves a problem of the valves known from U.S. Pat. No. 7,235,060, U.S. Pat. No. 7,559,912, US2010/0010415. There the rotor setting has to be locked or should be locked before and after the planned actuation of the rotor, because before and after actuation of the rotor it is not certain that the rotor will remain in the selected setting. Magnetic fields, in at least one possible embodiment electrically generated magnetic fields, are considered to be the principal cause. EP 1 380 317 proposes that the rotor be locked with a flexible housing that in the locking position presses in a frictional locking manner against the rotor casing. To release the lock, the housing is deformed such that it bulges laterally and releases the rotor for adjustment. The release is, however, not the same as an adjustment. For the adjustment the previously mentioned magnets have to be activated.

The processor and the data storage unit are in one possible embodiment combined in one unit. This will be referred to hereinafter as the data processing unit.

In at least one possible embodiment of the present application, a pressure gauge for measuring the liquor pressure and/or a temperature gauge for measuring the liquor temperature may be provided together, wherein the pressure gauge and/or temperature gauge is/are coupled with the data processing unit, such that the pressure measurement signals are recorded in the data processing unit and can be compared with a set point from the memory, in order to actuate or to keep the valve closed until the liquor pressure has reached the pre-set value.

Some devices that are suitable pressure gauges are described in DD289197 A5, DE102006004523 A1, DE102006004523 A1, DE102005020569 B4, DE102004056757 A1, DE102004056756 A1, DE102004055220 A1, DE29705671 U1, DE20121938 U1, DE20121388 U1, DE19713266 A1, DE19705474 A1, DE19638813 C1, DE196009983 C1, DE10353144 A1, DE10156469 B4, DE10156469 A1, DE10053409 C.

In one possible embodiment, pressure gauge chips are used in which an electrically conducting system reacts to pressure changes with a change in resistance for the flow of current.

In this way the pressure gauge can be designed such that the measurement signals occur in digital form or a signal converter can be provided between the pressure gauge and the data processing unit or can be provided on the pressure gauge or on the data processing unit.

At the same time a position detector is possible. The position detector is then also coupled with the data processing unit, such that the signals from the position detector can be recorded in the data processing unit, in order to switch the processor from one mode of operation to the other mode of operation. In this regard, one mode of operation is set up for the upright position and the other mode of operation is set up for the supine position.

A switch to at least one other intermediate mode of operation is also optionally provided, such that at least one transitional mode is provided between the upright position and the supine position.

A gliding adaptation to a position change can also optionally occur.

One possible device with a housing is suitable as a position detector in which a ball takes up another position that depends on the position of the patient and in which the position of the ball is measured. The position can be determined with contacts that for example on touching the ball exert by their resistance different influences on the flow of current. A position sensor is also suitable which comprises a housing with an eccentrically arranged disc that assumes another position depending on the patient position and for which, depending on the position of the disc, different electrical contacts are affected, such that different effects on the current flow are caused that depend on the position of the disc.

A micro-electromechanical system is in one possible embodiment used for the determination of the position which works on the basis of a change in capacitance of condensers. These sensors are mostly spring-mass systems made from silicon, in which the "springs" are silicon rods that are a few μm wide and the mass is also made of silicon. Deflection caused by acceleration can cause a measurable change in the electrical capacity between the sprung suspended part and a rigid reference electrode. The total measurement range corresponds to a capacity change of a few pF, the changes being in the fF range. The electronics for the interpretation of these small changes in capacity are integrated on the same semiconductor component. The condensers are arranged in three principal planes, by which the completely three-dimensional functioning can be determined for each position or change in position.

In this way the position detector can be designed such that the measurement signals occur in digital form or a signal converter can be provided between the position detector and the data processing unit or can be provided on the position detector or on the data processing unit.

Furthermore, additional conditions of the patient which have an influence on the liquor drainage or on the hydrocephalus treatment can be measured with measurement devices, wherein the measurement devices are coupled with the data processing unit, such that the signals from the measurement device can be recorded in the data processing unit in order to switch the processor over from one mode of operation to the other mode of operation. Such conditions can essentially ensure and/or promote as a function of the degree of suffering of the patient which causes the disorder of the liquid formation or for the disorder of the liquid flow or for the disorder of the liquor resorption. Such conditions can be inter alia blood pressure and heart rate.

Furthermore, certain demands from a physical activity or from a physical resting phase can be recorded in the data processing unit's program.

Various measurement devices can optionally be combined with each other.

A computer controlled hydrocephalus valve is already known from DE 10105315 A1. An electromechanical valve is described therein that is actuated by a programmable computerized control. The computerized control should be able to be programmed according to the differential pressure and optionally according to the position of the patient and according to the muscular potential and cerebral current.

DE1015315 A1 also teaches to implant the device in patients and to externally read the collected data and to carry out program modifications externally. This essentially requires and/or desires transmission and receiving devices.

DE 10105315 A1 also proposes a piezoelectric motion generation.

The realization of this known device with computer control has not been successful up to now, however.

For the realization of this known device there is now provided:

The position sensor/position detector transmits the posture of the patient to the control unit. The values measured by the pressure sensors/pressure gauge at the inlet and outlet can be utilized to realize short-term changes and to take them into account. Increasing high pressure changes occur very quickly with a change in position, which can be confirmed by the tilt sensor. Knowing the position of the patient, the control algorithm can now be adjusted. In the standing or sitting position the hydrostatic pressure is increased between the ventricle in the head and the drainage medium, the open period of the switch must or should therefore be shortened.

Slowly increasing pressure differences in an unchanged position of the patient indicate a rise in pressure in the brain. If in a given period a value pre-defined as critical is reached, without the patient having changed his position, then this can be evaluated as an increase in the brain pressure and the switch is consequently opened.

An optimal adjustment of the open period can be computed from the hydrostatic level, the pressure situation at the inlet and outlet of the drainage as well as from the viscosity of the liquid. The acquisition of the absolute pressure before and after the switch provides reference points for the actual drainage situation. For example, if a patient stands up when the switch is closed, then this leads both above and also below the switch to characteristic conditions that can be appropriately controlled.

Sensor data/measurement data and time data from the running insert can be saved. The saved data from the valve memory can be read out over the transmitter module and introduced into the diagnosis. The pressure difference at the switch can be used to determine the actual amount of liquid flow, in that it is related to the open period, the viscosity of the liquid as well as the geometry of the drainage. These data enable an adequate approximation of the amount of liquor flow to be calculated.

Saving such data to memory and the subsequent read out for the extra-corporal preparation offers the possibility to incorporate such findings into the diagnoses and therapy in general as well as in the case of incidents. Comparisons over the longer term enable conclusions to be drawn on the course of the disease and for the construction of improved control algorithms or corrections. Typical curves obtained individually from the afflicted patient can be incorporated into the algorithm. The comparison of the currently measured event with saved typical values can demonstrate pathological anomalies that result in a systematic intervention of the control algorithm.

In the communication between physician and patient, an optimal drainage profile can be drawn up as a function of observations, habits and medical requirements, and can be introduced to the implant, systematically checked for its effectiveness and optionally adjusted. In this way a great number of revisions may be avoided and/or minimized and/or reduced, which would have been required and/or desired by the previous state of the art.

Programming can be carried out by externally qualified personnel such that a function of the implanted valve can be manufactured according to the patient's needs. Thus there is the possibility for example to carry out an adaptation to modifications associated with growth or to program treatment profiles for certain specific forms of hydrocephalus.

The power consumption can be possibly reduced by switching functions on and off during operation.

A reduced power consumption is a key question for manufacturer and user in order to essentially ensure and/or promote a long service life for the implanted unit. Firstly this must or should be essentially ensured and/or promoted by the technical realization; secondly the physician should also have the possibility to limit energy-intensive examinations to immediate needs and/or desires. The physician should be able to select a low energy continuous operation and still be able to carry out short intensive examinations. A "burst mode" can be employed for this, which in high clock rates, in one possible embodiment one Hertz, evaluates data on pressure, temperature, valve setting and position for a short period of in one possible embodiment ten to twenty minutes and transmits the results to the control apparatus.

A programmable hydrocephalus valve has already been described in DE 10105315 which, by the use of a time switch for the opening conditions, enables a modifiable drainage of excess liquor. The valve switch is controlled electromagnetically by a lateral displacement of a ball out of the valve seat. In DE 10233601 two shape memory wires acting in opposing directions function as the actuator in order to laterally displace a ball and thereby to control the valve. In both cases the actuators are in direct contact with the liquid. Materials and contacts must or should therefore be biocompatible; moreover an electric and in one possible embodiment also thermal insulation is essentially required and/or desired. Despite the technical feasibility of both of the above-mentioned principles, a time-controlled valve has not yet been developed to achieve market approval. Long-term stability of the insulation and encapsulation of the parts that are in contact with the liquor as well as of the electric wiring is technically difficult to realize and makes the construction too complicated. One possible problem in operation is the high energy consumption that negatively impacts the requirement for a very long, maintenance-free functioning of the implant. The heat development linked to this also leads to problems associated with contact to the liquor. Even the further development of the shape memory drive in WO 20100066438, in which the wires do not come into contact with the liquor, does not resolve these problems.

By introducing a new kind of piezoelectrically driven switch, the present application now enables the realization of an electronically controlled and electrically driven valve type.

An essential component of the present application is the valve unit comprising a piezoelectric drive and a mechanical switch mechanism for opening and closing the drainage. This opening mechanism of the valve comprising a housing, a lever as the force or path transmission and a valve seat that is closed by a sealing body over the lever. The lever acts as the force or path transmission unit for a linear piezo actuator that is in one possible embodiment used here. With piezo actuators, high forces can be achieved with comparatively low strokes, the displacement of the actuator used here being two micrometers up to ten micrometers. That the information in DE 10105315 A1 has still not found any practical implementation, may be due to the short displacement path. The adjustment path of a piezo actuator is approximately linearly proportional to the voltage, i.e. by choosing a suitable voltage, an adaptation to individual patients' needs can be produced. Although the lever path that is achievable with the piezo actuator is indeed small, according to the present application the high force available with the piezo actuator is utilized in order to obtain by conversion a greater path that is essentially required and/or desired to open a valve. The conversion is obtained by a lever mechanism. The conversion can be chosen over a wide range at will. The opening slit can thereby be designed to be bigger or smaller independently of the position of the patient. Thus, for example, when the patient is standing a very small slit can be opened (zero voltage) and when the patient is reclining a higher liquor drainage can be set (maximum voltage). In accordance with medical specifications, other slits can also be incorporated. The control of the opening slit for regulating the typical low hydrocephalus flow rates is consequently possible without difficulty. The conversion is in one possible embodiment effected by a lever mechanism. The lever mechanism is optionally formed by a two-armed lever. A lever bearing belongs to the lever.

The width of the opening of the valve is constructively determined by the conversion that can be realized with a ratio of in one possible embodiment in the range of about 1:2 to about 1:10.

The lever bearing can be formed by a conventional pivot bearing.

In at least one possible embodiment of the present application, however, the lever bearing is formed by an elastic membrane. The membrane can be formed by a separate component. However, the membrane can also be designed with the lever in one piece.

This membrane is capable of at least the following functions: It can be used
1. as a bearing of the lever.
2. as a return spring that brings the unstressed lever into its clear starting position and
3. as a seal for the interior of the valve against the external space.

The lever axle therefore lays in a bearing-forming membrane that forces a kinematic fixing of the rotation axis and thereby forms an elastic bearing for the lever mechanism. With a twin armed lever, one lever arm is arranged on one side of the membrane and the other lever arm on the other side of the membrane. The piezo actuator is in one possible embodiment of the present application located on the short lever arm and the longer lever arm acts on the valve. The effective ratio of the lever arms determines the conversion ratio. The opening width of the valve is then determined by the deflection of the longer part of the lever; the lever ratio/conversion ratio being greater than the deflection of the piezo actuator.

The valve can have various designs.

For example it can be a ball valve or a membrane valve or a check valve or a cone valve.

A valve is in one possible embodiment provided with a ball-cone pair. This variant has proven its worth for hydrocephalus valves and is employed in numerous existing products (DE 19535637). In principle the seat can also be designed differently, for example needle shaped, cone shaped or planar.

The ball is led into the valve seat and is in one possible embodiment not connected to the lever. As soon as the valve is opened by the lever, the inlet-side over-pressure of the liquor creates a corresponding slit in the ball-cone pair and the liquid can flow. The elastic membrane automatically causes the recovery once the piezo actuator is switched off. In the starting position the ball is in one possible embodiment under pre-tension in the valve seat. Moreover, the lever is designed in such a way that the ball is pressed back into the conical valve seat. The pre-tensioning of the lever in the neutral position, i.e. with a closed valve, serves to essentially ensure and/or promote a tightly sealed seat of the ball even in the case of shocks.

The valve in one possible embodiment possesses two spaces that are hermetically separated by the membrane. One space is the valve interior, in the above case the space with the ball-cone. When the valve is opened the liquor will flow through the space. The other space is designated as an available space. The space in one possible embodiment comprises:
  the electrical components,
  the battery and
  the piezo actuator.

The liquor flowing through the interior of the valve is directed over the outlet into the abdominal cavity.

The installation space encapsulates the parts located therein, such that the installation space then also renders biocompatibility to the enclosed parts if these parts are not biocompatible without encapsulation.

The encapsulation also essentially prevents and/or minimizes and/or reduces any ingress of liquid into the installation space and the movement of liquid with the piezo actuator.

Electrical components are in one possible embodiment located in the installation space. The insulation of electric wires between the valve interior space and the installation space can then be dispensed with. The encapsulation then also provides an electrical insulation and essentially prevents and/or minimizes and/or reduces any danger to the patients which could result from the required and/or desired peak voltages of up to one hundred fifty volts.

The membrane that forms the bearing is in one possible embodiment welded to the inside of the valve housing. This causes a form fit and cohesive connection. Once welded, as also in other connections, the membrane partitions the housing and is tightly connected to it. It forms the pivot bearing for the lever.

For applications with other boundary conditions than those described here or for the use of another actuator with a greater adjustment travel, the lever lengths a:b can be selected fundamentally in three dependencies:
  $a<b$
  $a=b$
  $a>b$ In at least one possible embodiment of the present application, the lever bearing or whose membrane with the spatial separation (media separation) between electronics and the medium flowing through is applicable in the case of a conversion and also in a conversion of 1:1 or even with a reduction of the lever-drive movement.

The valve can also be opened in principle with other drives, for example by a solenoid or by a motor. Thus, drives can be designed for example by:
  piezo actuator (stack, bending actuator, etc.)
  DC motor, step, servo, torque motor
  solenoid
  MEMS, memory drives
  magnetostrictive actuators In at least one possible embodiment of the present application, a very low energy consumption is needed and/or desired with the use of a piezo actuator. In addition, in normal operation the piezo does not need and/or desire to be energized to afford complete deflection, thereby enabling the energy consumption to be further reduced. Maintaining a deflection requires and/or desires very little additional energy. This enables the lifetime of the implant to be significantly increased.

With the low energy consumption, the possible dissipation of energy into heat is also correspondingly low.

In order to protect the electronics, they are partially or completely encapsulated in, for example, polyurethane or epoxy resin. This can essentially prevent and/or minimize and/or reduce a short circuit or other dangers for the patient when the housing is deformed.

The battery is also in one possible embodiment implanted.

The voltage of the battery is selected between 2.8 and 3.2 volts. A 2.8 volt lithium-iodine battery, which is typically used in pacemakers, is in one possible embodiment employed. These types of battery are available for example from Greatbach Medical Company.

For a higher working voltage of the piezo actuator, the battery voltage is in one possible embodiment stepped up to the working voltage.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

An embodiment of the present application is illustrated in the drawings:

FIGS. 1A and 1B show an extracorporeal control unit;

DESCRIPTION OF EMBODIMENT OR EMBODIMENTS

Figure 2:
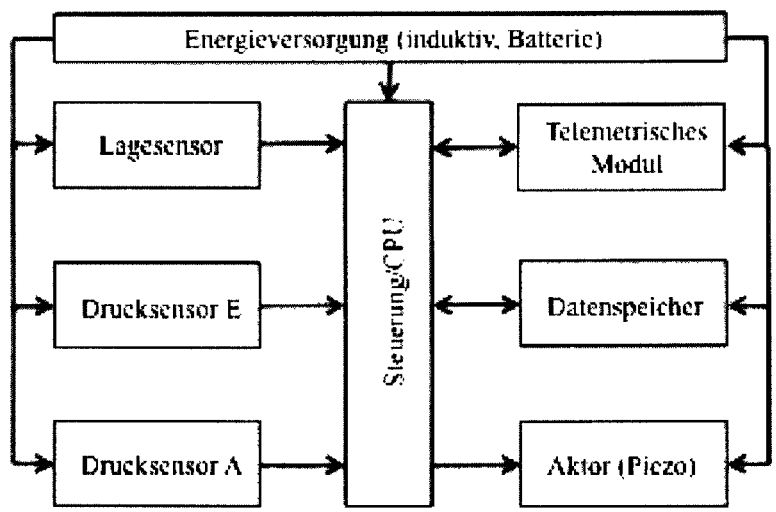
FIG. 2 shows a block diagram for clarifying the interaction of the control unit and implant.

FIGS. 1A and 1B show an extracorporeal control unit (control CPU) 1.0 and an implant 2.0 in a functional diagram with a list of the essential components. In FIG. 1B an external computer is illustrated as the configuration device 3.0.

The control unit 1.0 comprises a display 1.1, a battery 1.2, a transmitting and receiving unit (telemetric module) 1.3, a USB Com interface 1.4, a USB memory 1.5, an RF interface 1.6, a controller 1.7 and an absolute pressure sensor 1.8.

The implant 2.0 comprises a piezo actuated ball valve 2.1, a battery 2.2, a transmitting and receiving unit 2.3, a measurement device for the inlet pressure 2.4, a measurement device for the outlet pressure 2.5, a HV step, a controller 2.7 and an inclination measurer 2.8.

The battery 2.2 can be an inductively chargeable battery.

FIG. 2 shows a block diagram for clarifying the interaction of the control unit 1.0 and implant 2.0. This results in the control unit 1.0 communicating with the measurement devices of the implant and the piezo valve in the implant, wherein recourse is made both to saved data as well as new data that are saved.

Besides the programming, the control unit synchronizes data and time. The ID of the implant, the battery status and the operational mode are retrieved. The time is corrected/synchronized. In this regard, the worldwide time zones are supported. A significant exchange occurs continuously in regard to the quality of the telemetric link. For this, data and energy are visualized.

The implant can firstly be set up at the input device 3.0, which can be a computer, a smart-phone or a similar, mobile device. Secondly, the configurations transmitted from the reading device are selected. In at least one possible embodiment of the present application, this can be:

the set point of the valve status for a time period, in one possible embodiment twenty-four hours, the parameter for the individual adjustment of the posture-defined opening characteristics as well as the operational mode (data display, valve control mode, rapid data acquisition).

Figure 3:
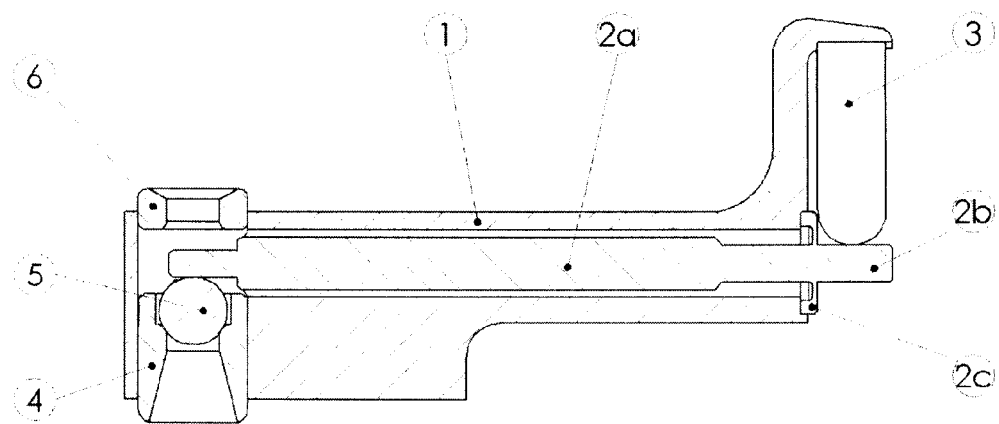
FIG. 3 shows details of the piezo valve.

FIG. 3 shows details of the piezo valve. The inlet 4 possesses a spherical valve seat, into which a valve ball 5 is fitted and rests opposite the outlet 6. The valve chamber housing 1 possesses a through hole, through which a lever arm 2a projects to the ball. The lever arm 2a bears down with its one end on the valve ball 5, the end being held by the elastic bearing 2c. The lever arm 2b projecting past the valve housing 1 is bent at an angle of 90 degrees. This reduces the construction volume of the valve. The smaller the valve, the greater the wearing comfort. The lever arm 2b is moved by means of a piezo actuator 3. A pivot bearing belongs to the swivel lever 2b. The pivot bearing is formed here by a membrane 2c. The membrane 2c simultaneously or substantially simultaneously separates the valve interior space from the exterior space. Moreover, the membrane forms a spring. The lever is returned to its starting position by the spring force. The membrane and the lever are at least partially finished on a lathe. The bent lever arm 2b is machined. The lever and the membrane have a circular cross section that enables their production on the lathe. In the embodiment, the membrane is made of titanium with a thickness of 0.18 millimeter and is welded to the valve chamber.

In other embodiments the bearing-forming membrane has an oval shape.

In still other embodiments the lever has a square, in another possible embodiment a rectangular cross section and a rectangular membrane.

These designs offer possibilities to match the shape of the valve housing to pre-defined geometric conditions.

In the illustrated embodiment the lever can be deformed with equal force in all or substantially all or most or some directions perpendicular or substantially perpendicular to the longitudinal direction. In order to essentially ensure and/or promote movement solely in one direction, a reinforcement can be formed on the bearing parallel or substantially parallel to the desired pivot axis of the lever. A bulge, for example, stiffens the bearing-forming membrane such that the desired curvature is created. The bulge runs in a plane, to which the drive movement of the piezo actuator is perpendicular or substantially perpendicular.

A similar effect to that of a bulge can also result from a groove that can be worked into the membrane.

A similar effect can also be produced by profiling the membrane. Thus, the membrane can also be undulating in shape in order to obtain a spring behavior that is as smooth as possible. This can be for cases, in which an exact or essentially exact valve seat is essential and/or desired. The axial compliance and therefore the displacement of the bearing axis during the positioning motion is optionally taken into account.

In other embodiments a biocompatible material other than titanium, optionally even plastic, is used. When the lever moves, such that the ball 5 is released, the ball is moved out of the valve seat by liquor resulting from overpressure, which opens the valve. A possible counter-pressure appearing on the outlet side when the switch is opened leads automatically to the closure of the valve by the ball being pressed from the medium into the valve seat 4, such that no return flow can occur.

In order to re-close the valve independently of the counter pressure, the voltage across the piezo actuator has to or should decrease. The ball 5 is again pressed into the valve seat against the inlet opening. This is effected primarily by the membrane 2c and secondarily by the lever 2a acting as the spring rod, which together form the spring system.

Figure 4:
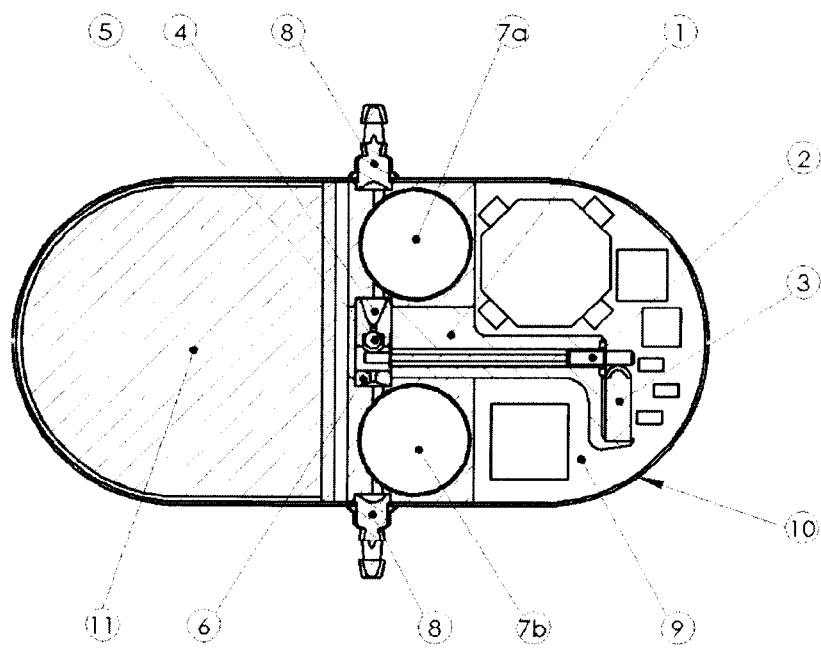
FIG. 4 shows an exploded view of the overall design of a valve of this type in a technical view.
Figure 5:
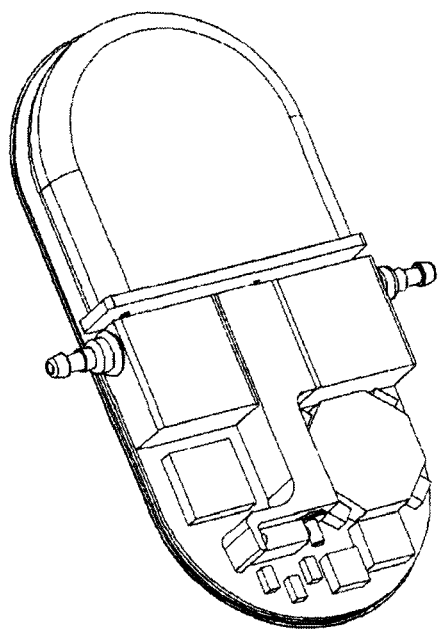
FIG. 5 shows a perspective partial view of a valve of this type in a technical view.

FIGS. 4 and 5 show (once in an exploded view, once in a perspective partial view) the overall design of a valve of this type in a technical view.

Here the membrane 2c is located between the two spaces in FIG. 3.

One space belongs to the flow channel of the liquor through the valve and in the embodiment touches the side of the membrane that faces the ball 5.

The other space touches the opposite side of the membrane and is designated here as the installation space.

The installation space is limited by the housing 10 that is in one possible embodiment made of titanium, in another possible embodiment TiAl6V4, as are the other metallic parts.

The left half of the installation space is filled by a battery 11. The energy required and/or desired to operate the piezo actuator is in one possible embodiment delivered by a small volume button battery. Even with low battery voltages of three volts for example, a piezoelectric spring displacement can be driven with operating voltages of up to one hundred fifty volts. The battery voltage is correspondingly transformed for this.

At the top center and the bottom center of the housing 10 are the inlet and outlet 8, which belong to the flow channel of the liquor through the valve. In the flow channel are two pressure sensors/pressure gauges with integrated temperature gauges 7a and 7b. Midway between the sensors/pressure gauges is the valve chamber 1, described in FIGS. 1A and 1B, again in one possible embodiment made of titanium. The piezo actuator 3 is located on the right. The remaining components are the controller for the program sequence, a positional sensor and a voltage converter, in order to produce the required and/or desired voltage for the piezo actuator from the battery voltage. These components are arranged in the remaining space 9.

A voltage across the piezo actuator 3 causes a displacement that deflects the lever 2 at its shorter end 2b. The displacement of the longer lever arm opens the valve, wherein the width of the opening is dependent on the applied voltage and on the lever step up or lever step down. The bore of the tapered seat 4 has a typical diameter of about one millimeter to two millimeters, in one possible embodiment 1.5 millimeters, for a ball diameter of typically 1.6 to 2.5 millimeters. With a low liquor viscosity a cone diameter of 0.5 millimeter can also be productive, wherein the ball diameter can then be between 0.7 and 1.5 millimeters. The ball 5 in one possible embodiment comprises a hard and light material, for example aluminum oxide ceramic. It has a somewhat larger, here in one possible embodiment about a 1.3 times larger diameter than the through hole of the tapered seat 4.

In FIG. 4 a specially processed area is provided underneath the housing. It is located opposite the plate with the coil for the inductive energy supply and telemetric data transfer. The housing wall is thinned out at this position so as to minimize the attenuation of the signal. In the illustrated embodiment the housing wall has been processed by removing material, wherein some cross pieces have been left for reasons of stability. In other embodiments the housing wall is formed by a welded on film. Films with a thickness of 0.012 millimeter to 0.1 millimeter are suitable for this purpose.

A programmable valve for the treatment of hydrocephalus is described. The present application comprises an implantable electrically controlled lever-operated valve and a programming and control device.

The implant has a power unit, a processor, a memory, a position sensor, pressure gauge, temperature sensor and an electric drive.

The lever is a swivel lever, whose drive is encapsulated with a membrane against the liquor.

One feature or aspect of an embodiment is believed at the time of the filing of this patent application to possibly reside broadly in an implantable hydrocephalus valve with an electrically operated valve, with a computer control that operatively connects with at least one pressure gauge, in one possible embodiment also operatively connected with a position detector, and compares the pressure gauge values and the inclination values with a pre-setting in order to actuate the valve in the event of a significant deviation, wherein a flow channel leads through the valve and wherein the closing devices of the valve are positioned in the flow channel wherein the actuation device for the valve comprises a lever mechanism and a drive mechanism, wherein at least one lever bearing is formed by a membrane that encapsulates at least the drive mechanism against the liquor.

Another feature or aspect of an embodiment is believed at the time of the filing of this patent application to possibly reside broadly in the device, wherein the membrane is firmly seated on the lever.

Yet another feature or aspect of an embodiment is believed at the time of the filing of this patent application to possibly reside broadly in the device, wherein the membrane is integrally formed with the lever.

Still another feature or aspect of an embodiment is believed at the time of the filing of this patent application to possibly reside broadly in the device, wherein the flow channel for the liquor extends to one side of the membrane and that the space that is encapsulated against the liquor extends to the other side of the membrane.

A further feature or aspect of an embodiment is believed at the time of the filing of this patent application to possibly reside broadly in the device, wherein the membrane forms the lever bearing.

Another feature or aspect of an embodiment is believed at the time of the filing of this patent application to possibly reside broadly in the device, wherein the lever mechanism is a step-up gear unit.

Yet another feature or aspect of an embodiment is believed at the time of the filing of this patent application to possibly reside broadly in the device, comprising a 2× to 10× step up of the drive movement.

Still another feature or aspect of an embodiment is believed at the time of the filing of this patent application to possibly reside broadly in a hydrocephalus valve according to the present application wherein the drive is formed by a piezo actuator.

A further feature or aspect of an embodiment is believed at the time of the filing of this patent application to possibly reside broadly in the device, wherein the drive is selected from the group of the DC motors, step motors, servo motors, torque motors.

Another feature or aspect of an embodiment is believed at the time of the filing of this patent application to possibly reside broadly in the device, wherein the drive is formed by a solenoid.

Yet another feature or aspect of an embodiment is believed at the time of the filing of this patent application to possibly reside broadly in the device, wherein the drive is selected from the group of the MEMS, memory drives.

Still another feature or aspect of an embodiment is believed at the time of the filing of this patent application to possibly reside broadly in the device, wherein the drive is formed as a magnetostrictive actuator.

A further feature or aspect of an embodiment is believed at the time of the filing of this patent application to possibly reside broadly in the device, comprising an electrical drive with a battery, in one possible embodiment an inductively chargeable battery.

One feature or aspect of an embodiment is believed at the time of the filing of this patent application to possibly reside broadly in the device, comprising a transformer device provided between battery and drive or on the device for increasing the battery voltage to the voltage of the drive.

Another feature or aspect of an embodiment is believed at the time of the filing of this patent application to possibly reside broadly in the device, wherein the device is configured to locate at least one pressure gauge in the flow direction of the liquor before and after the valve or in the valve.

Yet another feature or aspect of an embodiment is believed at the time of the filing of this patent application to possibly reside broadly in the device, comprising the use of pressure gauges with a digital measurement signal or a downstream converter for the measurement signal.

Still another feature or aspect of an embodiment is believed at the time of the filing of this patent application to possibly reside broadly in the device, wherein the device is configured to locate at least one position detector with a digital measurement signal or a downstream converter for the measurement signal before or after the valve or in the valve.

A further feature or aspect of an embodiment is believed at the time of the filing of this patent application to possibly reside broadly in the device, including locating at least one temperature measurement device with a digital measurement signal or a downstream converter for the measurement signal before or after the valve or in the valve.

Another feature or aspect of an embodiment is believed at the time of the filing of this patent application to possibly reside broadly in the device, comprising a processor and data memory device in the implant for the valve control and with a data link between the valve and the measurement devices.

Yet another feature or aspect of an embodiment is believed at the time of the filing of this patent application to possibly reside broadly in the device, comprising an implant with a data link between the valve and the measurement devices as well as a telemetric measurement value transmission to an external control apparatus that is equipped with processor and data memory device.

Still another feature or aspect of an embodiment is believed at the time of the filing of this patent application to possibly reside broadly in the device, comprising a programmable processor.

A further feature or aspect of an embodiment is believed at the time of the filing of this patent application to possibly reside broadly in the device, comprising a round, in one possible embodiment a circular cross section of the lever.

Another feature or aspect of an embodiment is believed at the time of the filing of this patent application to possibly reside broadly in the device, comprising a square cross section of the lever, in one possible embodiment a rectangular cross section of the lever.

Yet another feature or aspect of an embodiment is believed at the time of the filing of this patent application to possibly reside broadly in the device, comprising a—in the view along the lever—round, in one possible embodiment a circular bearing-forming membrane.

Still another feature or aspect of an embodiment is believed at the time of the filing of this patent application to possibly reside broadly in the hydrocephalus valve, comprising a—in the view along the lever—square, in one possible embodiment a rectangular bearing-forming membrane.

The components disclosed in the patents, patent applications, patent publications, and other documents disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications, patent publications, and other documents cited herein, and in the Declaration attached hereto, are hereby incorporated by reference as if set forth in their entirety herein except for the exceptions indicated herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, patent applications, patent publications, and other documents which are included in this application and which are referred to in paragraphs which state "Some examples of . . . which may possibly be used in at least one possible embodiment of the present application . . ." may possibly not be used or useable in any one or more embodiments of the application.

The sentence immediately above relates to patents, patent applications, patent publications, and other documents either incorporated by reference or not incorporated by reference.

U.S. patent application Ser. No. 12/981,224, filed on Dec. 29, 2010, having inventor Christoph MIETHKE and title "CEREBROSPINAL FLUID DRAINAGE", having Publication No. US 2011-0166495 A1, and its corresponding Federal Republic of Germany Patent Application No. 10 2008 030 942, filed on Jan. 7, 2010, and International Patent Application No. PCT/EP2009/004751, filed on Jul. 1, 2009, having WIPO Publication No. WO 2010/000461 and inventor Christoph MIETHKE are hereby incorporated by reference as if set forth in their entirety herein.

U.S. patent application Ser. No. 13/478,157, filed on May 23, 2012, having inventor Christoph MIETHKE and title "IMPLANTABLE HYDROCEPHALUS SHUNT SYSTEM", having Publication No. US 2012-0232462 A1, and its corresponding Federal Republic of Germany Patent Application No. 10 2009 060 533.9, filed on Dec. 23, 2009, and International Patent Application No. PCT/EP2010/007817, filed on Dec. 21, 2010, having WIPO Publication No. WO 2011/076382 and inventor Christoph MIETHKE are hereby incorporated by reference as if set forth in their entirety herein.

U.S. patent application Ser. No. 11/149,928, filed on Jun. 10, 2005, having inventor Christoph MIETHKE and title "METHOD OF TREATING A PATIENT WITH HYDROCEPHALUS AND APPARATUS THEREFOR", having Publication No. US 2007-0004999 A1, and its corresponding U.S. Pat. No. 7,422,566, issued on Sep. 9, 2008, and its corresponding Federal Republic of Germany Patent Application No. 103 47 278.9, filed on Oct. 8, 2003, and Federal Republic of Germany Patent Application No. 102 58 070.7, filed on Dec. 11, 2002, and International Patent Application No. PCT/EP03/13999, filed on Dec. 10, 2003, having WIPO Publication No. WO 2005/092424 and inventor Christoph MIETHKE are hereby incorporated by reference as if set forth in their entirety herein.

U.S. patent application Ser. No. 11/535,242, filed on Sep. 26, 2006, having inventor Christoph MIETHKE and title "ADJUSTABLE HYDROCEPHALUS VALVE", having Publication No. US 2007-0093741 A1, and its corresponding U.S. Pat. No. 7,766,855, issued on Aug. 3, 2010, and its corresponding Federal Republic of Germany Patent Application No. 10 2004 015 500.3, filed on Mar. 27, 2004, and International Patent Application No. PCT/EP05/03052, filed on Mar. 22, 2005, having WIPO Publication No. WO 2004/052443 and WIPO Publication No. 2005/092424 and inventor Christoph MIETHKE are hereby incorporated by reference as if set forth in their entirety herein.

U.S. patent application Ser. No. 13/866,730, filed on Apr. 19, 2013, having inventor Christoph MIETHKE and title "IMPLANT FOR MEASURING THE INTRACORPOREAL PRESSURE WITH TELEMETRIC TRANSMISSION OF THE MEASURED VALUE", and its corresponding Federal Republic of Germany Patent Application No. 10 2010 049 150.0, filed on Oct. 22, 2010, and International Patent Application No. PCT/EP2011/003903, filed on Aug. 4, 2011, having WIPO Publication No. WO 2012/065750 and inventor Christoph MIETHKE are hereby incorporated by reference as if set forth in their entirety herein.

All of the patents, patent applications, patent publications, and other documents, except for the exceptions indicated herein, which were cited in the International Search Report mailed Oct. 5, 2012, and/or cited elsewhere, as well as the International Search Report document itself, are hereby incorporated by reference as if set forth in their entirety herein except for the exceptions indicated herein, as follows: EP 2 008 683, having the title "Programmable shunt with electromechanical valve actuator", published on Dec. 31, 2008; EP 1 380 317, having title "Shunt valve locking mechanism", published on Jan. 14, 2004; and DE 201 21 938, having the English translation of the German title "Sensor device for measurement of pressure values inside epi- or subdural drainage systems within the human body has a leak-tight housing with a sensor arrangement that transmits measurement values to an external evaluation unit", published on Sep. 4, 2003.

The corresponding foreign and international patent publication applications, namely, Federal Republic of Germany Patent Application No. 10 2010 051 743.7, filed on Nov. 19, 2010, having inventor Christoph MIETHKE, and DE-OS 10 2010 051 743.7 and DE-PS 10 2010 051 743.7, and International Application No. PCT/EP2011/005819, filed on Nov. 18, 2011, having WIPO Publication No. WO 2012/065750 and inventor Christoph MIETHKE, are hereby incorporated by reference as if set forth in their entirety herein, except for the exceptions indicated herein, for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications, patent publications, and other documents, except for the exceptions indicated herein, are hereby incorporated by reference as if set forth in their entirety herein except for the exceptions indicated herein.

The purpose of incorporating the corresponding foreign equivalent patent application(s), that is, PCT/EP2011/005819 and German Patent Application 10 2010 051 743.7, is solely for the purposes of providing a basis of correction of any wording in the pages of the present application, which may have been mistranslated or misinterpreted by the translator, and to provide additional information relating to technical features of one or more embodiments, which information may not be completely disclosed in the wording in the pages of this application.

Statements made in the original foreign patent applications PCT/EP2011/005819 and DE 10 2010 051 743.7 from which this patent application claims priority which do not have to do with the correction of the translation in this patent application are not to be included in this patent application in the incorporation by reference.

Any statements about admissions of prior art in the original foreign patent applications PCT/EP2011/005819 and DE 10 2010 051 743.7 are not to be included in this patent application in the incorporation by reference, since the laws relating to prior art in non-U.S. Patent Offices and courts may be substantially different from the Patent Laws of the United States.

All of the references and documents cited in any of the patents, patent applications, patent publications, and other documents cited herein, except for the exceptions indicated herein, are hereby incorporated by reference as if set forth in their entirety herein except for the exceptions indicated herein. All of the patents, patent applications, patent publications, and other documents cited herein, referred to in the immediately preceding sentence, include all of the patents, patent applications, patent publications, and other documents cited anywhere in the present application.

Words relating to the opinions and judgments of the author of all patents, patent applications, patent publications, and other documents cited herein and not directly relating to the technical details of the description of the embodiments therein are not incorporated by reference.

The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments of the patents, patent applications, patent publications, and other documents, are not considered to be incorporated by reference herein for any of the patents, patent applications, patent publications, and other documents cited herein.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications, patent publications, and other documents cited herein may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72 (b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. Implantable hydrocephalus valve with an electrically operated valve, with a computer control being operatively connected with at least one pressure gauge, also operatively connected with a position detector configured to determine inclination values of a patient in which the valve is implanted, and being configured to compare pressure gauge values and inclination values with a pre-setting in order to actuate the valve in the event of a significant deviation, wherein a flow channel leads through the valve and wherein the valve comprises a closing device positioned in the flow channel, wherein the valve comprises an actuation device, which actuation device comprises a lever mechanism and a drive mechanism, wherein at least one lever bearing is formed by a membrane that encapsulates at least the drive mechanism against liquor in the valve.

2. The hydrocephalus valve according to claim 1, wherein either
the membrane is firmly seated on the lever; or
the membrane is integrally formed with the lever.

3. The hydrocephalus valve according to claim 2, wherein the flow channel for the liquor extends to one side of the membrane and that the space that is encapsulated against the liquor extends to the other side of the membrane.

4. The hydrocephalus valve according to claim 3, wherein the membrane forms the lever bearing.

5. The hydrocephalus valve according to claim 4, wherein said hydrocephalus valve comprises a 2-times to 10-times step up of a drive movement of the drive mechanism.

6. The hydrocephalus valve according to claim 5, wherein the drive comprises one of: a piezo actuator, a solenoid, a MEMS device, a memory drive, a magnetostrictive actuator, a DC motor, a step motor, a servo motor, or a torque motor.

7. The hydrocephalus valve according to claim 6, wherein said hydrocephalus valve comprises an electrical drive comprising a battery or an inductively chargeable battery.

8. The hydrocephalus valve according to claim 7, wherein said hydrocephalus valve comprises a transformer device for increasing the battery voltage to the voltage of the drive.

9. The hydrocephalus valve according to claim 8, wherein at least one pressure gauge is located in the flow direction of the liquor before and after the valve or in the valve.

10. The hydrocephalus valve according to claim 9, wherein said hydrocephalus valve comprises pressure gauges with a digital measurement signal or a downstream converter for the measurement signal.

11. The hydrocephalus valve according to claim 10, wherein at least one position detector with a digital measurement signal or a downstream converter for the measurement signal is located before or after the valve or in the valve.

12. The hydrocephalus valve according to claim 11, wherein at least one temperature measurement device with a digital measurement signal or a downstream converter for the measurement signal is located before or after the valve or in the valve.

13. The hydrocephalus valve according to claim 12, wherein said hydrocephalus valve comprises a processor and data memory device in the implant for the valve control and with a data link between the valve and the measurement devices.

14. The hydrocephalus valve according to claim 13, wherein said hydrocephalus valve comprises an implant with a data link between the valve and the measurement devices as well as a telemetric measurement value transmission to an external control apparatus that is equipped with processor and data memory device.

15. The hydrocephalus valve according to claim 14, wherein said hydrocephalus valve comprises a programmable processor.

16. The hydrocephalus valve according to claim 15, wherein said hydrocephalus valve comprises:
- one of (i) and (j), wherein (i) and (j) are:
  - (i) a round cross section of the lever, and
    a round bearing-forming membrane, in the view along the lever; and
  - (j) a circular cross section of the lever, and
    a circular bearing-forming membrane, in the view along the lever.

17. The hydrocephalus valve according to claim 15, wherein said lever comprises:
- a square cross section; and
- a square bearing-forming membrane, in the view along the lever.

18. The hydrocephalus valve according to claim 15, wherein said lever comprises:
- a rectangular cross section, and
- a rectangular bearing-forming membrane, in the view along the lever.

* * * * *